United States Patent
Wang et al.

(10) Patent No.: US 11,609,175 B2
(45) Date of Patent: Mar. 21, 2023

(54) METHOD AND DEVICE FOR IDENTIFYING PLATELET AGGREGATION AND CELL ANALYZER

(71) Applicant: SHENZHEN MINDRAY BIO-MEDICAL ELECTRONICS CO., LTD., Shenzhen (CN)

(72) Inventors: Guanzhen Wang, Shenzhen (CN); Bo Ye, Shenzhen (CN); Jiantao Di, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 542 days.

(21) Appl. No.: 16/719,850

(22) Filed: Dec. 18, 2019

(65) Prior Publication Data
US 2020/0132589 A1 Apr. 30, 2020

Related U.S. Application Data

(63) Continuation of application No. PCT/CN2017/089159, filed on Jun. 20, 2017.

(51) Int. Cl.
*G01N 15/14* (2006.01)
*G01N 1/28* (2006.01)
(Continued)

(52) U.S. Cl.
CPC ........... *G01N 15/1429* (2013.01); *G01N 1/28* (2013.01); *G01N 1/30* (2013.01); *G01N 15/1434* (2013.01);
(Continued)

(58) Field of Classification Search
CPC ........ G01N 15/1429; G01N 1/28; G01N 1/30; G01N 15/1434; G01N 33/5094;
(Continued)

(56) References Cited

U.S. PATENT DOCUMENTS

| 6,525,807 B1 | 2/2003 | Morikawa et al. |
| 10,281,458 B2 * | 5/2019 | Masuda ............. G01N 21/6428 |

(Continued)

FOREIGN PATENT DOCUMENTS

| CN | 101046439 A | 10/2007 |
| CN | 104515723 A | 4/2015 |

(Continued)

OTHER PUBLICATIONS

Extended European search report in related European Application No. 17914544.6, dated May 26, 2020, 12 pages.

*Primary Examiner* — Roy M Punnoose
(74) *Attorney, Agent, or Firm* — Kory D. Christensen

(57) ABSTRACT

The present invention falls within the field of medical apparatuses. Disclosed are a method and a device for identifying platelet aggregation, and a flow cytometer, which are used for accurately giving an alarm about a platelet aggregation during blood cell analysis. The method comprises: detecting a pre-treated blood sample by using a flow cytometry technique so as to acquire scattered light signals and fluorescent light signals of the blood sample, wherein the scattered light signals are forward scattered light signals or side scattered light signals; differentiating between ghost particles and white blood cells by using a fluorescence-scattered light diagram generated by the scattered light signals and the fluorescent light signals of the blood sample; and counting a number of particles in a ghost characteristic region in the fluorescence-scattered light diagram of the blood sample and determining whether the number of particles exceeds a threshold value, and outputting a warning of platelet aggregation if the number of particles exceeds the threshold value.

17 Claims, 10 Drawing Sheets

(51) Int. Cl.
  *G01N 1/30* (2006.01)
  *G01N 33/50* (2006.01)
(52) U.S. Cl.
  CPC . *G01N 33/5094* (2013.01); *G01N 2015/1486* (2013.01)
(58) Field of Classification Search
  CPC ... G01N 2015/1486; G01N 2015/1461; G01N 15/1459; G01N 15/00; G01N 33/00; C12Q 1/00
  See application file for complete search history.

(56) References Cited

U.S. PATENT DOCUMENTS

| | | | | |
|---|---|---|---|---|
| 2007/0231913 | A1* | 10/2007 | Tsuji | G01N 15/1459 436/63 |
| 2008/0176274 | A1* | 7/2008 | Tsuji | G01N 33/52 435/34 |
| 2009/0111118 | A1* | 4/2009 | Mylvaganam | G01N 33/80 435/6.11 |
| 2010/0248300 | A1* | 9/2010 | Yoshida | G01N 15/1459 435/39 |
| 2014/0011232 | A1* | 1/2014 | Vidal | G01N 27/02 435/39 |
| 2017/0074863 | A1* | 3/2017 | Masuda | G01N 1/38 |

FOREIGN PATENT DOCUMENTS

| | | | | |
|---|---|---|---|---|
| CN | 105986003 | A | 10/2016 | |
| CN | 106483109 | A | 3/2017 | |
| CN | 106525666 | A | 3/2017 | |
| CN | 106662572 | A | 5/2017 | |
| CN | 106687810 | A | 5/2017 | |
| CN | 106687810 | B | 10/2019 | |
| EP | 3136081 | A1 | 3/2017 | |
| EP | 3141885 | A1 * | 3/2017 | ............... G01N 1/30 |
| JP | 2007263894 | A | 10/2007 | |
| JP | 4484375 | B2 | 6/2010 | |
| WO | WO-2004001408 | A1 * | 12/2003 | ............ G01N 33/52 |
| WO | 2016127364 | A1 | 8/2016 | |

* cited by examiner

METHOD AND DEVICE FOR IDENTIFYING PLATELET AGGREGATION AND CELL ANALYZER

TECHNICAL FIELD

The present invention relates to the field of medical equipment, specifically to a method and a device for identifying platelet aggregation and a cell analyzer, and in particular to a method, a device and a cell analyzer for identifying platelet aggregation by utilizing a ghost characteristic region in a scatterdiagram generated by scattered light signals and fluorescence signals.

BACKGROUND ART

Platelets have no cell nucleus and are derived from megakaryocytes. Unactivated Platelets are biconvex discoid structures. Platelets are fragments of cytoplasm containing granules and having a cell membrane, and platelets have an average diameter of 2.4 μm and an average volume of 7.2 fL. Under normal conditions, the platelets circulate in the form of individual cells in blood vessels and do not interact with other types of cells and other platelets. When the endothelial layer is damaged and subendothelial matrix components such as collagen are exposed, the platelets can adhere onto the damaged vascular endothelium and stick to each other for producing thrombin. Finally fibrinogen is changed into fibrin through the produced platelet thrombus and thrombin, thereby achieving hemostasis. Platelets are mainly involved in hemostasis and thrombosis in vivo, having very important physiological functions, so platelet count is one of the most common tests performed clinically.

A blood cell analyzer is an instrument that is capable of detecting cells in blood, which is used to count and classify white blood cells (WBCs), red blood cells (RBCS), platelets (Ms), nucleated red blood cells (NRBCs), reticulocytes and other cells. If the results provided by the blood cell analyzer show that a patient suffers from thrombocytopenia, then doctors may be instructed to take bone marrow examination or transfuse platelets for treatment on the patient. The phenomenon of pseudoreduction in the number of platelets counted by the blood cell analyzer due to platelet aggregation is called pseudothrombocytopenia. Pseudothrombocytopenia has been widely reported, and its causative factors are various, including EDTA-dependent factor, cold-induced aggregation factor and drug-induced factor that have been reported. Among them, EDTA-dependent pseudothrombocytopenia is the most widely reported and studied. It is reported that the causative factor may be induced by EDTA-dependent antiplatelet antibodies, but the mechanism of its occurrence is still unknown. Pseudothrombocytopenia is hard to discover due to its low incidence and is thus very prone to missed diagnosis.

However, if this phenomenon cannot be identified, it can lead to clinical misdiagnosis and even wrong treatment, especially when a patient needs surgery or chemotherapy, the result of pseudothrombocytopenia may lead to delay or even cessation of treatment with serious consequences.

At present, the main methods for counting platelets with blood cell analyzers include impedance and optical methods. When platelet aggregation (PLT aggregation) occurs, two or more platelets aggregate together, with morphological characteristics similar to those of large cells (such as white blood cells). Hence, platelet aggregates have characteristics that are rather similar to those of large cells (such as white blood cells) when passing through the detection device, whether in the voltage information by the impedance method or the scattered light or fluorescence information by the optical method, making it impossible to distinguish therebetween and to provide accurate warnings.

Therefore, there is an urgent need for an accurate method and device for identifying platelet aggregation so as to give warnings of PLT aggregation accurately during blood cell analysis.

SUMMARY OF THE INVENTION

For avoiding the defects in the prior art, the present invention provides a method and a device for identifying platelet aggregation, which can output accurate warning of PLT aggregation during blood cell analysis, thereby helping operators to interpret results of a blood cell analyzer and avoiding the occurrence of pseudothrombocytopenia.

In order to realize the purpose of the present invention, the present invention applies the following technical solutions.

A method for identifying platelet aggregation comprises the steps of:

detecting a pretreated blood sample by using a flow cytometry technique so as to acquire scattered light signals and fluorescence signals of the blood sample, wherein the scattered light signals are forward scattered light signals or a side scattered light signals;

differentiating between ghost particles and white blood cells by using a fluorescence-scattered light scatterdiagram formed by the scattered light signals and the fluorescence signals of the blood sample; and counting a number of particles in a ghost characteristic region in the fluorescence-scattered light scatterdiagram of the blood sample to determine whether the number of particles exceeds a threshold value, and outputting a warning of platelet aggregation if the number of particles exceeds the threshold value.

In the method, the pretreatment comprises hemolyzing and fluorescence staining of cells in the blood sample.

In the method, the ghost characteristic region is a part of a ghost region.

Further, the ghost characteristic region is determined based on a position of a white blood cell population region.

Further, the ghost characteristic region is a region in the ghost region in which the scattered light signals are equal to and/or greater than the scattered light signals of the white blood cell population and the fluorescence signals are equal to and/or greater than the fluorescence signals of the white blood cell population.

Further, the threshold value is preset according to the selection of the ghost characteristic region.

Accordingly, the present invention also provides a device for identifying platelet aggregation, comprising:

an optical signal acquisition unit for acquiring scattered light signals and fluorescence signals generated by cells in a blood sample when passing through a detection region of a flow cytometer, wherein the scattered light signals are forward scattered light signals or side scattered light signals;

a scatterdiagram generating unit for generating a fluorescence-scattered light scatterdiagram according to the scattered light signals and the fluorescence signals to differentiate between ghost particles and white blood cells in the blood sample; and an analysis and warning unit for acquiring a ghost characteristic region of the fluorescence-scattered light scatterdiagram of the blood sample, counting a number of particles in the ghost characteristic region to determine whether the number of particles exceeds a threshold value, and outputting a warning of platelet aggregation if the number of particles exceeds the threshold value.

In the device, the analysis and warning unit comprises:

a ghost characteristic region determination unit for analyzing a ghost region in the fluorescence-scattered light scatterdiagram to determine the ghost characteristic region, wherein the ghost characteristic region is a part of the ghost region.

Further, the analysis and warning unit comprises:

a ghost characteristic region determination unit for analyzing a ghost region of the fluorescence-scattered light scatterdiagram to determine the ghost characteristic region, wherein the ghost characteristic region is determined based on a position of a white blood cell population region.

Further, the analysis and warning unit comprises:

a ghost characteristic region determination unit for analyzing a ghost region in the fluorescence-scattered light scatterdiagram to determine the ghost characteristic region, wherein the ghost characteristic region is a region in the ghost region in which the scattered light signals are equal to and/or greater than the scattered light signals of a white blood cell population and the fluorescence signals are equal to and/or greater than the fluorescence signals of the white blood cell population.

In the device, the analysis and warning unit further comprises:

a counting unit for counting the number of particles in the ghost characteristic region;

a comparison unit for comparing the number of particles in the ghost characteristic region with a predetermined threshold value;

a determination unit for determining that a platelet aggregation exists in the blood sample when the number of particles in the ghost characteristic region is greater than the predetermined threshold value; and a warning unit for giving a warning after determining that a platelet aggregation exists in the blood sample.

In another aspect, the present invention also provides a cell analyzer, comprising:

a sampling device for drawing a blood sample;

a pretreatment device for pretreatment of the blood sample so as to obtain a treated blood sample, wherein the pretreatment comprises hemolyzing and fluorescence staining of cells in the blood sample;

a detection device for passing the cells in the treated blood sample one by one through a detection region to detect scattered light signals and fluorescence signals of the cells in the blood sample, wherein the scattered light signals are forward scattered light signals and/or side scattered light signals; and an above-described device for identifying platelet aggregation, used for generating a fluorescence-scattered light scatterdiagram of the blood sample according to the forward scattered light signals, the side scattered light signals and the fluorescence signals detected by the detection device, acquiring a ghost characteristic region of the fluorescence-scattered light scatterdiagram and counting a number of particles in the ghost characteristic region to determine whether the number of particles exceeds a threshold value, and outputting a warning of platelet aggregation if the number of particles exceeds the threshold value.

Accordingly, the present invention also provides a computer-readable storage medium, comprising instructions which, when executed on a computer, cause the computer to perform the above method for identifying platelet aggregation.

By implementing the present application, the following beneficial effects can be achieved:

In the present application, a blood sample is pretreated with a reagent, and cells in the blood sample are detected via a flow cytometer so as to obtain scattered light signals and fluorescence signals of the cells. By generating a fluorescence-scattered light scatterdiagram, ghost particles and white blood cells in the blood sample are distinguished from each other, and a number of particles in a specific region within a ghost region is obtained to determine whether PLT aggregation exists in the blood sample, thereby identifying and warning the existence of PLT aggregation. In the present application, so long as NRBCs and WBCs can be distinguished from each other in a common channel, the identification of PLT aggregation can be carried out by using a specific region in the ghost region without employing a special pretreatment reagent, and a more accurate PLT aggregation warning can be given, thereby providing important information for clinical blood cell analysis in a quick and simple manner without increasing the structure and cost of the instrument system.

BRIEF DESCRIPTION OF THE DRAWINGS

In order to more clearly explain embodiments of the present invention or technical solutions in the prior art, a brief introduction to the drawings required for the description of the embodiments or the prior art is provided below.

DETAILED DESCRIPTION OF EMBODIMENTS

In order to facilitate the understanding of the present application, some technical terms involved in the present application are explained first as following.

A scatterdiagram is a two-dimensional plot generated by a flow cytometer, in which two-dimensional characteristic information of particles is distributed, wherein an X-axis and a Y-axis of the scatterdiagram each represent a characteristic of each particle. For example, in a scatterdiagram, the X-axis represents the intensity of fluorescence while the Y-axis represents the intensity of forward scattered light.

A cell population is a particle population, such as a white blood cell population, formed by a plurality of particles with the same characteristics and distributed in a certain region of the scatterdiagram.

NRBC channel: after a blood sample is treated with a fluorescent reagent, nucleated red blood cells can be classified and the NRBC channel can provide a white blood cell count and a nucleated red blood cell count.

The NRBC channel of a blood cell analyzer can independently detect nucleated red blood cells and provide a white blood cell count and a nucleated red blood cell count. Red blood cells and platelets are treated with a hemolytic agent and a fluorescent dye to form ghost fragments, thereby generating a ghost region via detection of an optical system. In addition, some components inside red blood cells and platelets, such as cytochrome and riboflavin, would bind with the fluorescent dye, thus generating fluorescence signals. Moreover, due to different sizes of the ghost particles, the ghost particles generate forward scattered light signals that vary in magnitude. Due to different complexity of the ghost particles, the ghost particles generate side scattered light signals that vary in magnitude.

After in-depth research, the applicant analyzed a large amount of forward scattered light, side scattered light and fluorescence information collected from PLT aggregation blood samples, and found that the number of particles within a specific region in a ghost region of a fluorescence-forward scattered light scatterdiagram or a fluorescence-side scattered light scatterdiagram is closely related to PLT aggregation, By measuring the number of particles within the characteristic region in the ghost region, whether PLT aggregation exists in the blood sample can be determined for PLT aggregation identification and warning.

Figure 1:
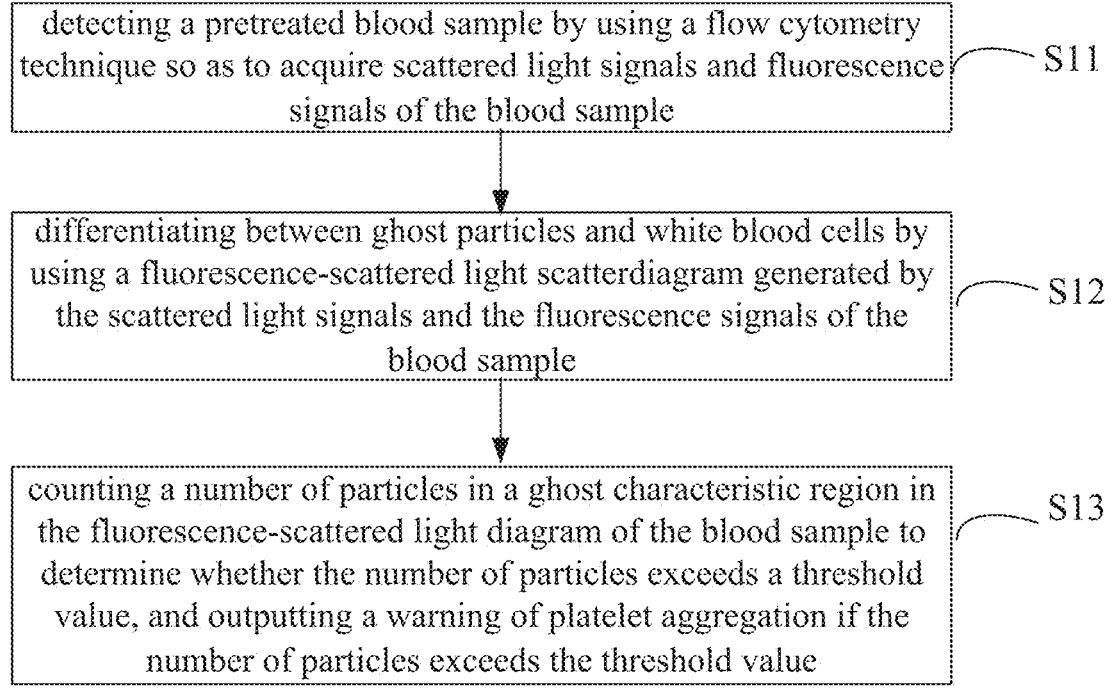
FIG. 1 is a flow chart of an embodiment of a method for identifying platelet aggregation provided in the present application.

As shown in FIG. 1, a method for identifying platelet aggregation provided by the present application comprises the steps of:

at S11, detecting a pretreated blood sample by using a flow cytometry technique so as to acquire scattered light signals and fluorescence signals of the blood sample, wherein the scattered light signals are forward scattered light signals or side scattered light signals;

at S12, differentiating between ghost particles and white blood cells by using a fluorescence-scattered light scatterdiagram formed by the scattered light signals and the fluorescence signals of the blood sample; and at S13, counting a number of particles in a ghost characteristic region in the fluorescence-scattered light scatterdiagram of the blood sample and determining whether the number of particles exceeds a threshold value, and if the number of particles exceeds the threshold value, outputting a warning of platelet aggregation.

It can be understood that in the method for identifying platelet aggregation of the present invention, the blood sample needs to be pretreated before the detection. The pretreatment comprises hemolyzing and fluorescence staining of cells in the blood sample.

Specifically, the blood sample is mixed with a hemolytic reagent and a fluorescent dye according to a certain mixing ratio to prepare a treated blood sample. The hemolytic reagent can lyse red blood cells and platelets in the blood sample to form ghost particles, so as to be differentiated from white blood cells and nucleated red blood cells, while the fluorescent dye binds with nucleic acids in white blood cells and nucleated red blood cells and with cytochrome, riboflavin, etc. inside the red blood cells and platelets, thereby labeling the cells. Different fluorescence information would be generated due to the difference in the binding ability of the fluorescent dye with the nucleic acids in the white blood cells and nucleated red blood cells and the cytochrome, riboflavin, etc. in the red blood cells and platelets.

The pretreated blood sample described in step S11 passes through the flow cytometer such that the scattered light signals and fluorescence signals can be collected when cells pass through a detection region one by one.

The scattered light signals are the light scattered to the whole space by cells that are irradiated by a laser beam when passing through a detection region one by one, including forward scattered light and side scattered light. The forward scattered light reflects information about the cell size, while the side scattered light reflects the complexity of the internal structure of cells. Therefore, different forward scattered light information would be generated due to different sizes of various types of cells, and different side scattered light information would be generated due to different morphology or complexity in cells.

The scattered light signals and fluorescence signals are acquired from measurement data of the same channel of the flow cytometer, i.e. the channel for differentiating NRBCs and WBCs, for example, the NRBC channel of a BC-6800 cell analyzer of Shenzhen Mindray Bio-Medical Electronics Co., Ltd.

It can be understood that the forward scattered light signals, the side scattered light signals and the fluorescence signals of cells in a blood sample can be simultaneously obtained in one test, that is, when the cells pass through the detection region of the flow cytometer, the forward scattered light signals, the side scattered light signals and the fluorescence signals of the cells in the blood sample are simultaneously collected. These signals can also be obtained through multiple tests. For example, the treated blood sample can be divided into two identical portions. The first portion of the blood sample is injected into the flow cytometer, and each cell in the first portion passes through the detection region of the flow cytometer so as to detect and collect a forward scattered light signal and a fluorescence signal of each cell in the first portion of blood sample; and then the second portion of the blood sample is injected into the flow cytometer, and each cell in the second portion passes through the detection region of the flow cytometer so as to detect and collect a side scattered light signal and a fluorescence signal of each cell in the second portion of blood sample.

In step S12, the fluorescence signals collected in S11 are indicated along the X-axis and the scattered light signals collected in S11 are indicated along the Y-axis to obtain a fluorescence-scattered light scatterdiagram, and the fluorescence-scattered light scatterdiagram is used to distinguish between ghost particles, nucleated red blood cells and white blood cells.

In the Step S13, for counting a number of particles in the ghost characteristic region in the fluorescence-scattered light scatterdiagram of the blood sample, it is necessary to first determine the position and size of the ghost characteristic region. The position and size of the ghost characteristic region vary with the position and size of the ghost region and the white blood cell population in the fluorescence-scattered light scatterdiagram.

In the method, the ghost characteristic region is a part of the ghost region. The ghost characteristic region is a specific region of the ghost region that is referred to as the ghost characteristic region. For example, a specific region of the ghost region, the scattered light signals of which are greater than a specific signal value and/or the fluorescence signals are greater than a specific signal value, may be taken as the ghost characteristic region. Alternatively, a specific region of the ghost region, the scattered light signals of which are equal to a specific signal value and/or the fluorescence signals are equal to a specific signal value may be taken as the ghost characteristic region. Alternatively, a specific region of the ghost region, the scattered light signals of which are less than a specific signal value and/or the fluorescence signals are less than a specific signal value may be taken as the ghost characteristic region.

Further, in some embodiments, the ghost characteristic region is determined based on a position of the white blood cell population region. That is, the ghost characteristic region is a specific region in the ghost region determined according to scattered light signals and fluorescence signals of the white blood cell population region.

Specifically and further, the ghost characteristic region is a region in the ghost region in which the scattered light signals are equal to and/or greater than the scattered light signals of the white blood cell population and the fluorescence signals are equal to and/or greater than the fluorescence signals of the white blood cell population.

It can be understood that in one embodiment, the ghost characteristic region is a region in the ghost region in which the scattered light signals are equal to and greater than the scattered light signals of the white blood cell population and the fluorescence signals are equal to and greater than the fluorescence signals of the white blood cell population. That is, the white blood cell population region and the ghost region are firstly distinguished from each other according to the fluorescence-scattered light scatterdiagram, and a lower boundary and a left boundary of the ghost characteristic region are determined by the minimum signal scattered light and the minimum fluorescence signal of the white blood cell population on the fluorescence-scattered light scatterdiagram, and then the region that overlaps with the ghost region is selected as the ghost characteristic region in the ghost region according to the lower boundary and the left boundary of the white blood cell population region. That is, the scattered light signals of the ghost characteristic region are greater than or equal to the minimum scattered light signal of the white blood cell region and the fluorescence signals of the ghost characteristic region are greater than or equal to the fluorescence signals of the white blood cell region.

In one embodiment, the ghost characteristic region is a region in the ghost region in which the scattered light signals are greater than the scattered light signals of the white blood cell population and the fluorescence signals are greater than the fluorescence signals of the white blood cell population. That is, the white blood cell population region and the ghost region are firstly distinguished from each other according to the fluorescence-scattered light scatterdiagram, and a lower boundary and a left boundary of the ghost characteristic region are determined by the maximum scattered light signal and the maximum fluorescence signal of the white blood cell population on the fluorescence-scattered light scatterdiagram, and then the region in the ghost region that overlaps with the ghost region is selected as the ghost characteristic region according to the lower boundary and the left boundary of the ghost characteristic region. That is, the scattered light signals of the ghost characteristic region are greater than or equal to the maximum scattered light signal of the white blood cell region, and the fluorescence signals of the ghost characteristic region are greater than or equal to the maximum fluorescence signal of the white blood cell region.

In one embodiment, the ghost characteristic region is a region in the ghost region in which the scattered light signals are equal to the scattered light signals of the white blood cell population and the fluorescence signals are equal to the fluorescence signals of the white blood cell population, That is, the white blood cell population region and the ghost region are firstly distinguished from each other according to the fluorescence-scattered light scatterdiagram, and an upper boundary, a lower boundary, a left boundary and a right boundary of the ghost characteristic region are respectively determined by the maximum scattered light signal, the minimum light scatter signal, the maximum fluorescence signal and the minimum fluorescence signal of the white blood cell population on the fluorescence-scattered light scatterdiagram, and then the region in the ghost region that overlaps with the ghost region is selected as the ghost characteristic region according to the upper boundary, the lower boundary, the left boundary and the right boundary of the ghost characteristic region. That is, the scattered light signals of the ghost characteristic region are greater than or equal to the minimum scattered light signal of the white blood cell region and less than or equal to the maximum scattered light signal of the white blood cell region, or the fluorescence signals of the ghost characteristic region are greater than or equal to the minimum fluorescence signal of the white blood cell region and less than or equal to the maximum fluorescence signal of the white blood cell region.

Similarly, the ghost characteristic region can also be selected from a region in the ghost region in which the scattered light signals are equal to and greater than the scattered light signals of the white blood cell population and the fluorescence signals are greater than the fluorescence signals of the white blood cell population, a region in the ghost region in which the scattered light signals are greater than the scattered light signals of the white blood cell population and the fluorescence signals are equal to and greater than the fluorescence signals of the white blood cell population, a region in the ghost region in which the scattered light signals are equal to the scattered light signals of the white blood cell population and the fluorescence signals are equal to and greater than the fluorescence signals of the white blood cell population, a region in the ghost region in which the scattered light signals are equal to and greater than the scattered light signals of the white blood cell population and the fluorescence signals are equal to the fluorescence signals of the white blood cell population, a region in the ghost region in which the scattered light signals are equal to the scattered light signals of the white blood cell population and the fluorescence signals are greater than the fluorescence signals of the white blood cell population, or a region in the ghost region in which the scattered light signals are greater than the scattered light signals of the white blood cell population and the fluorescence signals are equal to the fluorescence signals of the white blood cell population.

It can be understood that in step S12, alternatively, the scattered light signals collected in S11 can be indicated along the X-axis, and the fluorescence signals collected in S11 can be indicated along the Y-axis to obtain a corresponding fluorescence-scattered light scatterdiagram, and the fluorescence-scattered light scatterdiagram can be further used to distinguish between ghost particles, nucleated red blood cells and white blood cells. In addition, the position and size of the ghost characteristic region in step S13 will be changed according to the position and size of the ghost region and the white blood cell population in the corresponding fluorescence-scattered light scatterdiagram.

Further, in the step S13, the number of particles in the ghost characteristic region in the fluorescence-scattered light scatterdiagram of the blood sample is counted and compared with a threshold value to determine whether the number of particles exceeds the threshold value. If the counted number of particles in the ghost characteristic region is greater than the predetermined threshold value, it is determined that platelet aggregation appears in the blood sample and a warning is output.

The warning is output in a form of text, sound, light or a pop-up window, etc.

The threshold value is a fixed value preset according to experimental statistics.

Those skilled in the art can properly adjust the position of the predetermined ghost characteristic region according to statistical experiments of actual threshold values to enhance the accuracy of platelet aggregation identification and warning.

It is to be understood that the alphanumeric designations of the above steps are merely for convenience and do not limit the sequence of the steps.

The term "scatterdiagram" as used herein can be a visualized graph or a set of non-visualized data, as long as it enables the method above to be implemented.

The method for identifying platelet aggregation described in the present application mainly uses the ghost characteristic region in a scatterdiagram generated by scattered light signals and fluorescence signals.

Figure 2:
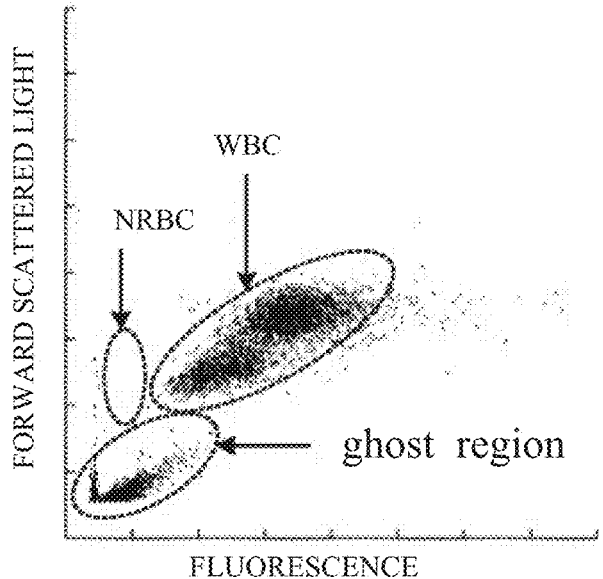
FIG. 2 is a fluorescence-forward scattered light scatterdiagram of a normal sample.
Figure 3:
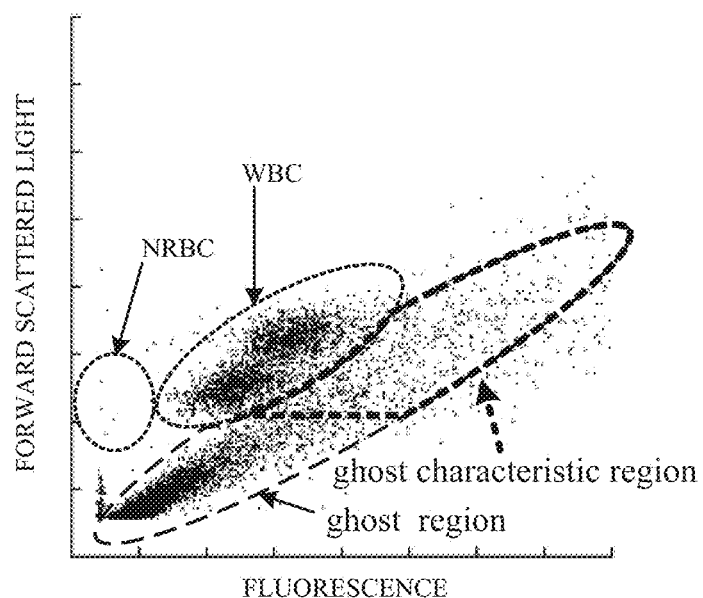
FIG. 3 is a fluorescence-forward scattered light scatterdiagram of a PLT aggregation sample.

Specifically, in a particular embodiment of the present application, a normal sample and a PLT aggregation sample are compared with each other. The normal sample and the PLT aggregation sample are respectively pretreated with a fluorescent dye reagent described in Embodiment 10 of Chinese Patent CN 200910238927. Then, the pretreated blood samples are tested by a BC-6800 cell analyzer of Shenzhen Mindray Bio-Medical Electronics Co., Ltd. by the method described previously using a flow cytometry technique to obtain forward scattered light signals and fluorescence signals of the normal sample and forward scattered light signals and fluorescence signals of the PLT aggregation sample, respectively. According to the collected forward scattered light information and fluorescence information of the normal sample, a fluorescence-forward scattered light scatterdiagram of the normal sample is generated, a ghost region and a white blood cell population are distinguished from each other, and a region in the ghost region in which the forward scattered light signals are equal to and greater than the forward scattered light signals of the white blood cell population and the fluorescence signals are equal to and greater than the fluorescence signals of the white blood cell population is selected as the ghost characteristic region (as shown in FIG. 2). According to the collected forward scattered light information and fluorescence information of the PLT aggregation sample, a fluorescence-forward scattered light scatterdiagram of the PLT aggregation sample is generated, a ghost region and a white blood cell population are distinguished from each other, and a region in the ghost region in which the forward scattered light signals are equal to and greater than the forward scattered light signals of the white blood cell population and the fluorescence signals are equal to and greater than the fluorescence signals of the white blood cell population is selected as the ghost characteristic region (as shown in FIG. 3). Numbers of particles in the ghost characteristic region of the normal sample and the PLT aggregation sample are counted respectively and compared with a preset threshold value, and PLT aggregation can be identified according to whether the number of particles exceeds the threshold value.

In order to further confirm the effect of the method for identifying platelet aggregation provided in the embodiments of the present application, the applicant conducted a series of comparative experiments. The applicant randomly selected 4 normal samples and 28 PLT aggregation samples, wherein it was confirmed by manual microscopic examination of blood smears that no PLT aggregation existed in any of the normal samples; and it was confirmed by manual microscopic examination of blood smears that PLT aggregation existed in all the PLT aggregation samples. Through the platelet identification method described in this application, the above 4 normal samples and 28 PLT aggregation samples were tested respectively, and no PUT aggregation warning was given for any of the 4 normal samples, while a PLT aggregation warning was given for all the 28 PLT aggregation samples.

Figure 4:
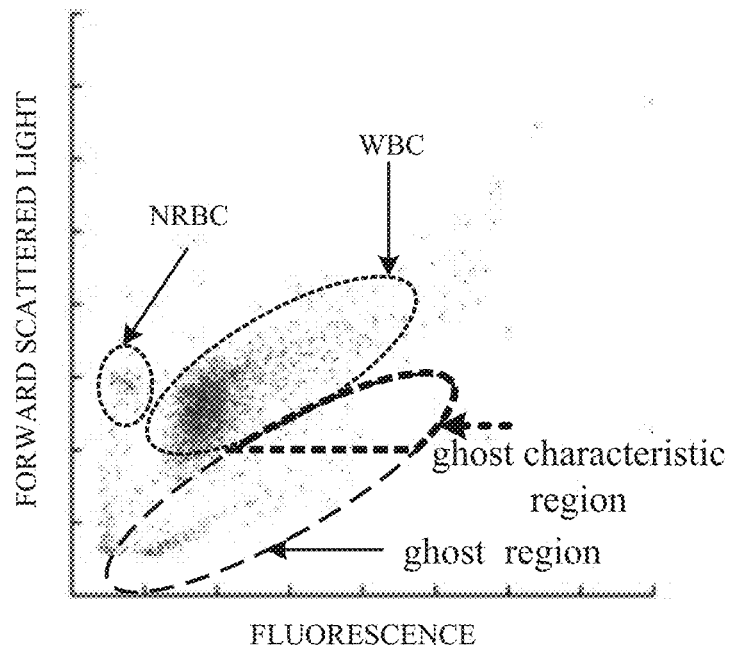
FIG. 4 is a fluorescence-forward scattered light scatterdiagram of a PLT aggregation sample detected by a BC-6800 cell analyzer after being pretreated with another fluorescence staining reagent.

In a particular embodiment of the present application, a PLT aggregation sample pretreated with another fluorescent dye reagent (said another fluorescent dye reagent is composed of a fluorescent dye compound shown by formula I, hydrochloric acid, glycine, citric acid, dodecyl trimethyl ammonium bromide, cocoamidopropyl betaine and ethylenediamine tetraacetic acid, with a pH value of 2.9) is used. The pretreated blood sample is tested by a BC-6800 cell analyzer of Shenzhen Mindray Bio-Medical Electronics Co., Ltd. by the method described previously using a flow cytometry technique to obtain forward scattered light signals and fluorescence signals of the PLT aggregation sample. According to the collected forward scattered light information and fluorescence information, a fluorescence-forward scattered light scatterdiagram of the PLT aggregation sample is generated (FIG. 4), and a ghost region and a white blood cell population are distinguished from each other. A region in the ghost region in which the forward scatter signals are equal to and greater than the forward scattered light signals of the white blood cell population and the fluorescence signals are equal to and greater than the fluorescence signals of the white blood cell population is selected as the ghost characteristic region, Number of particles in the ghost characteristic region of the normal sample and the PLT aggregation sample are counted respectively and compared with a preset threshold value, and PLT aggregation can be identified according to whether the number of particles exceeds the threshold value,

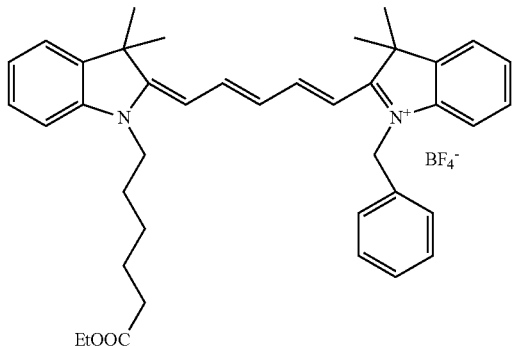

I

It can be seen that with different reagents used in the pretreatment step, whether PLT aggregation exists in the blood sample can be determined finally, without exception, by measuring the number of particles within the ghost characteristic region in the ghost region and thus PLT aggregation identification and warning can be carried out.

Figure 7:
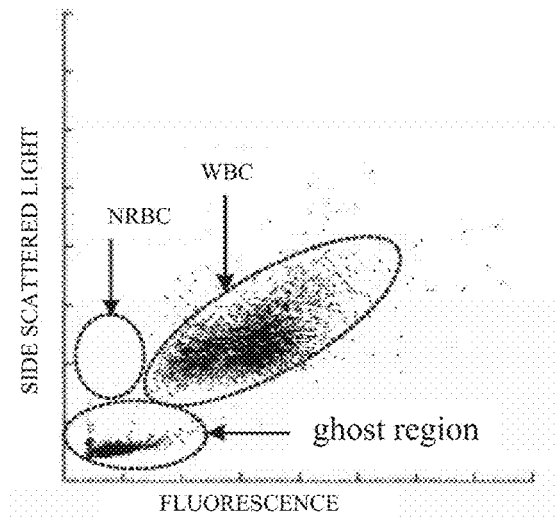
FIG. 7 is a fluorescence-side scattered light scatterdiagram of a normal sample.
Figure 8:
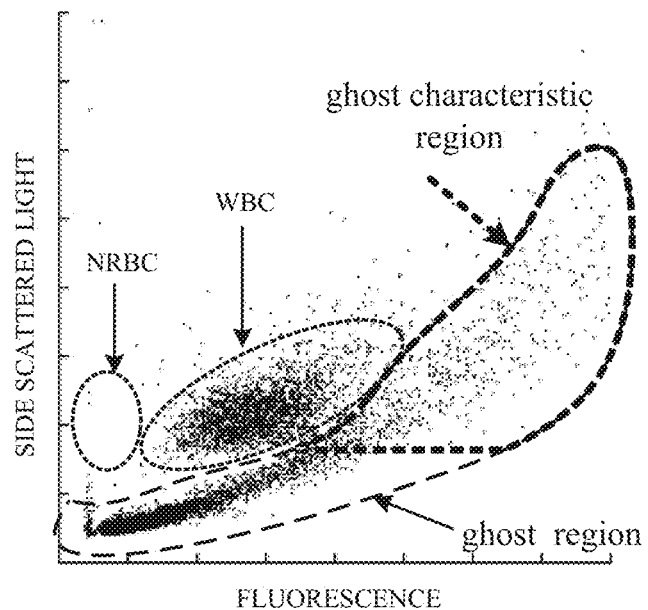
FIG. 8 is a fluorescence-side scattered light scatterdiagram of a PLT aggregation sample.

In another particular embodiment of the present application, a normal sample and a PLT aggregation sample are compared with each other. The normal sample and the PLT aggregation sample are respectively pretreated with a fluorescent dye reagent of a compound described in Embodiment 10 of Chinese Patent CN 200910238927. Then, the pretreated blood samples are tested by a BC-6800 cell analyzer of Shenzhen Mindray Bio-Medical Electronics Co., Ltd. by the method described previously using a flow cytometry technique to obtain side scattered light signals and fluorescence signals of the normal sample and side scattered light signals and fluorescence signals of the PLT aggregation sample, respectively. According to the collected side scattered light information and fluorescence information of the normal sample, a fluorescence-side scattered light scatterdiagram of the normal sample is generated, a ghost region and a white blood cell population are distinguished from each other, and a region in the ghost region in which the side scattered light signals are equal to and greater than the side scattered light signals of the white blood cell population and the fluorescence signals are equal to and greater than the fluorescence signals of the white blood cell population is selected as the ghost characteristic region (as shown in FIG. 7). According to the collected side scattered light information and fluorescence information of the PLT aggregation sample, a fluorescence-side scattered light scatterdiagram of the PLT aggregation sample is generated, a ghost region and a white blood cell population are distinguished from each other, and a region in the ghost region in which the side scattered light signals are equal to and greater than the side scattered light signals of the white blood cell population and the fluorescence signals are equal to and greater than the fluorescence signals of the white blood cell population is selected as the ghost characteristic region (as shown in FIG. 8). Numbers of particles in the ghost characteristic region of the normal sample and the PLT aggregation sample are counted respectively and compared with a preset threshold value, and PLT aggregation can be identified according to whether the number of particles exceeds the threshold value.

In order to further confirm the effect of the method for identifying platelet aggregation provided in the embodiments of the present application, the applicant conducted a series of comparative experiments. The applicant randomly selected 4 normal samples and 28 PLT aggregation samples, wherein it was confirmed by manual microscopic examination of blood smears that no PLT aggregation existed in any of the normal samples; and it was confirmed by manual microscopic examination of blood smears that PLT aggregation existed in all the PLT aggregation samples. Through the platelet identification method described in this application, the above 4 normal samples and 28 PLT aggregation samples were tested respectively, and no PLT aggregation warning was given for any of the 4 normal samples, while a PLT aggregation warning was given for all the 28 PLT aggregation samples.

Figure 9:
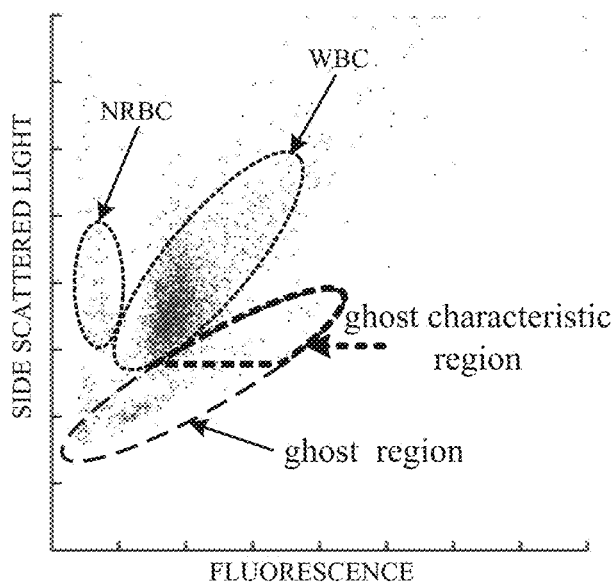
FIG. 9 is a fluorescence-side scattered light scatterdiagram of a PLT aggregation sample detected by a BC-6800 cell analyzer after being pretreated with another fluorescence staining reagent.

Similarly, in a particular embodiment of the present application, a PLT aggregation sample pretreated with another fluorescent dye (said another fluorescent dye reagent is composed of a fluorescent dye compound shown by formula I, hydrochloric acid, glycine, citric acid, dodecyl trimethyl ammonium bromide, cocoamidopropyl betaine and ethylenediamine tetraacetic acid, with a pH value of 2.9) is used. The pretreated blood sample is tested by a BC-6800 cell analyzer of Shenzhen Mindray Bio-Medical Electronics Co., Ltd. by the method described previously using a flow cytometry technique to obtain side scattered light signals and fluorescence signals of the PLT aggregation sample. According to the collected side scattered light information and fluorescence information, a fluorescence-side scattered light scatterdiagram of the PLT aggregation sample is generated (FIG. 9), and a ghost region and a white blood cell population are distinguished from each other. A region in the ghost region in which the side scattered light signals are equal to and greater than the side scattered light signals of the white blood cell population and the fluorescence signals are equal to and greater than the fluorescence signals of the white blood cell population is selected as the ghost characteristic region, Numbers of particles in the ghost characteristic region of the normal sample and the PLT aggregation sample are counted respectively and compared with a preset threshold value, and PLT aggregation can be identified according to whether the number of particles exceeds the threshold value.

It can be seen that with different laser beam collection angles (forward scattered light or side scattered light) employed, whether PLT aggregation exists in a blood sample can be determined, without exception, by measuring the number of particles within the ghost characteristic region in the ghost region and thus PLT aggregation identification and warning can be carried out.

Further, the above results show that identification of platelet aggregation in blood samples using the method provided by this application has higher warning sensitivity and specificity and better warning accuracy.

It can be understood that the method according to the embodiments of the present application can be implemented by a flow cytometer and a host computer thereof, and more specifically can be implemented by means of running software. In addition, it can be understood that the method provided by the embodiments of the present application is not directly related to the reagent used and the irradiation angle of the laser beam, and the ghost characteristic region can be determined as long as ghost particles and white blood cells can be clearly distinguished from each other in the fluorescence-scattered light scatterdiagram.

Figure 12:
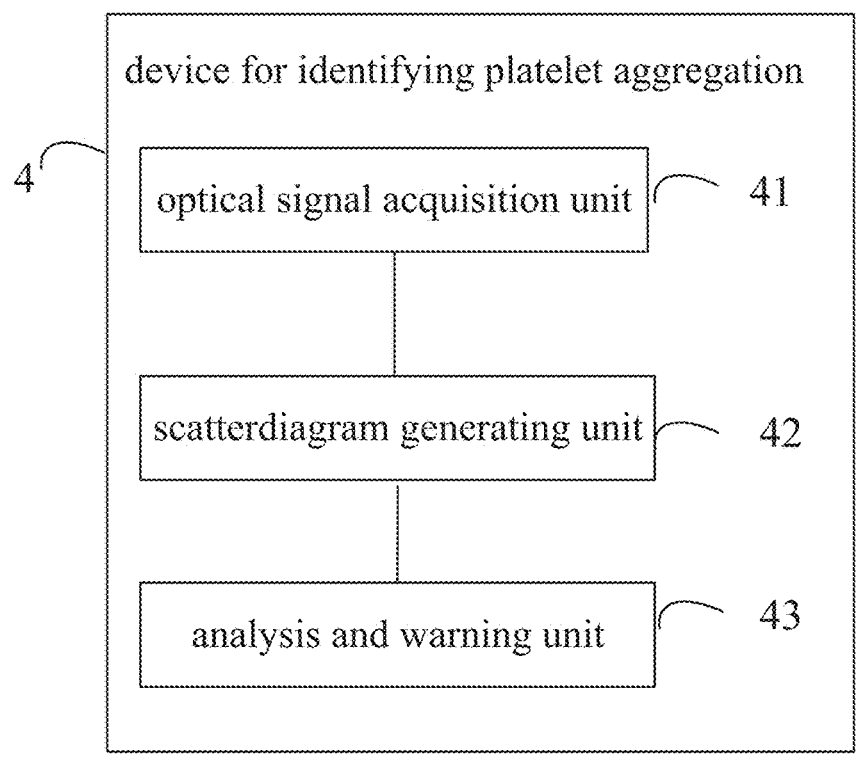
FIG. 12 is a schematic structure diagram of an embodiment of a device for identifying platelet aggregation provided in the present application.
Figure 13:
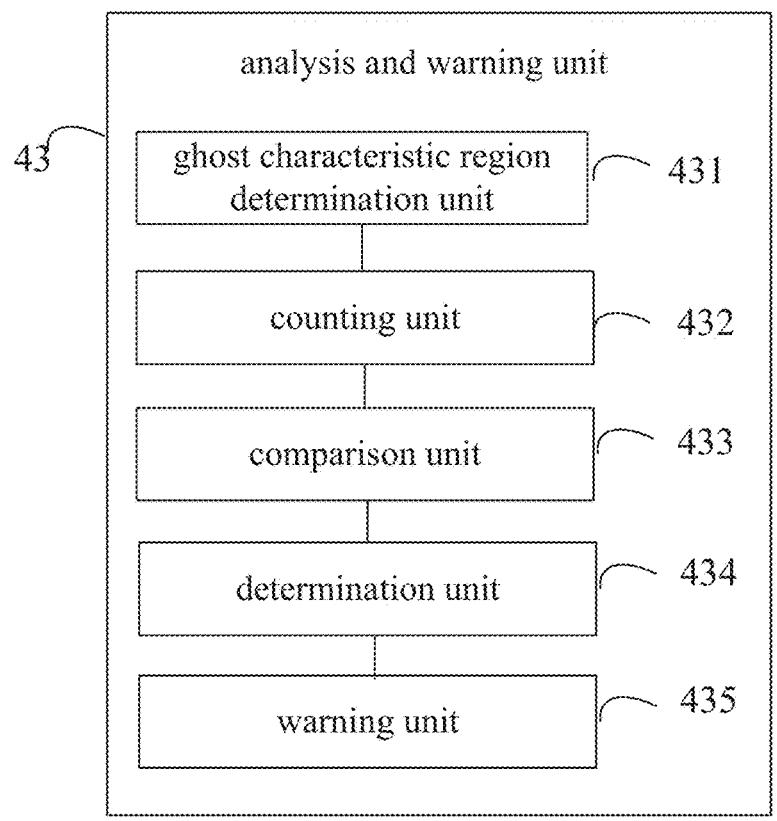
FIG. 13 is a schematic structure diagram of an analysis and warning unit in FIG. 12.
Figure 14:
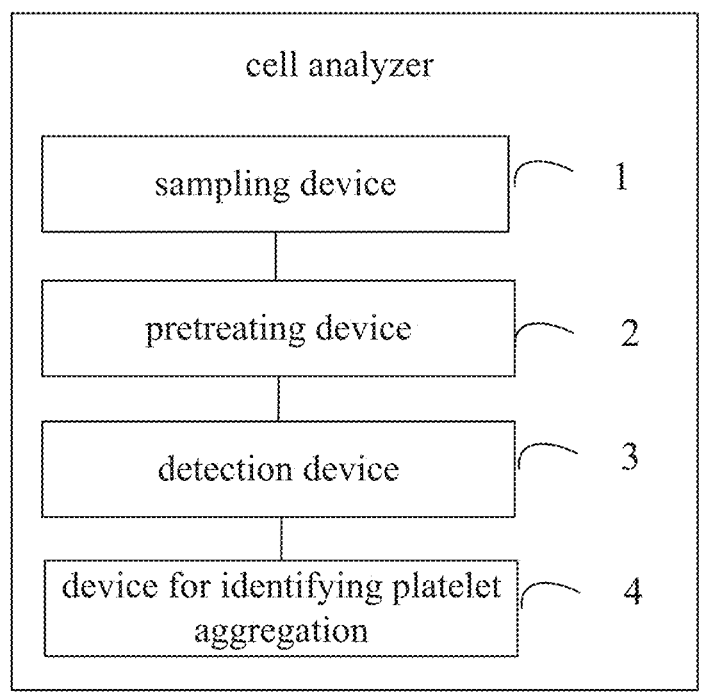
FIG. 14 is a schematic structure diagram of one embodiment of a flow cytometer provided in the present application.
Figure 15:
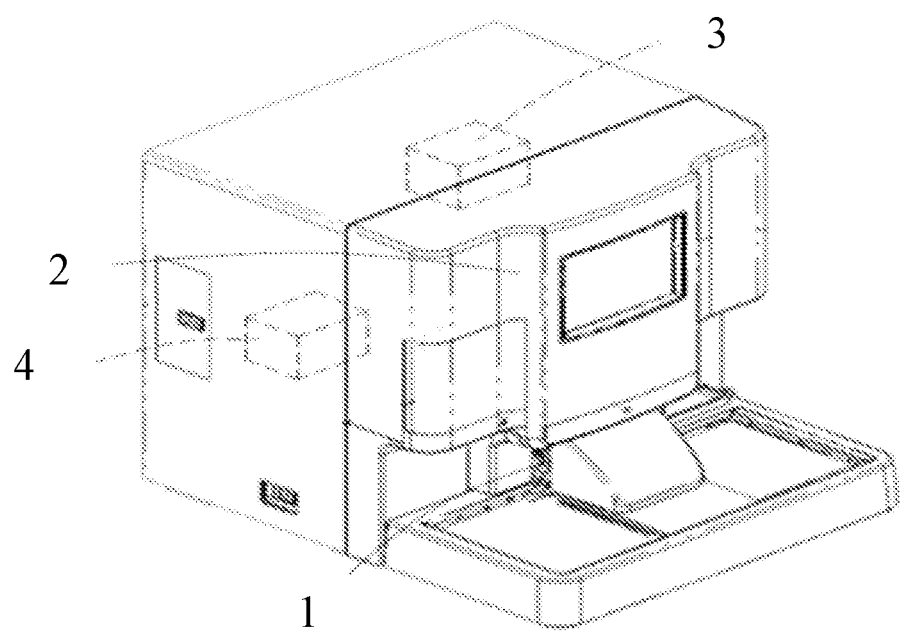
FIG. 15 is a schematic structure diagram of a BC-6800 cell analyzer provided in the present application.

The present application also provides a device for identifying platelet aggregation. As depicted in FIGS. 12 to 14, an embodiment of a device for identifying platelet aggregation is shown. In this embodiment, the device 4 for identifying platelet aggregation is used for give warnings with regard to whether platelet aggregation exists in a blood sample, and comprises:

an optical signal acquisition unit 41 for acquiring scattered light signals and fluorescence signals of cells in a blood sample when passing through a detection region of a flow cytometer, wherein the scattered light signals are forward scattered light signals or side scattered light signals; and specifically, the optical signal acquisition unit 41 acquires signals from measurement data of the same channel of the flow cytometer, i.e., acquires the forward scattered light signals, the side scattered light signals and the fluorescence signals of the cells in the blood sample from the channel for differentiating between NRBCs and WBCs;

a scatterdiagram generating unit 42 for generating a fluorescence-scattered light scatterdiagram according to the scattered light signals and the fluorescence signals acquired by the optical signal acquisition unit 41 to differentiate between ghosts particles and white blood cells in the blood sample; and an analysis and warning unit 43 for acquiring a ghost characteristic region of the fluorescence-scattered light scatterdiagram of the blood sample, counting a number of particles in the ghost characteristic region to determine whether the number of particles exceeds a threshold value, and outputting a warning of platelet aggregation if the number of particles exceeds the threshold value.

Specifically, the analysis and warning unit 43 comprises:

a ghost characteristic region determination unit 431 for analyzing a ghost region of the fluorescence-scattered light scatterdiagram to determine the ghost characteristic region, wherein the ghost characteristic region is a part of the ghost region;

a counting unit 432 for counting the number of particles in the ghost characteristic region;

a comparison unit 433 for comparing the number of particles in the ghost characteristic region with a predetermined threshold value;

a determination unit 134 for determining that platelet aggregation exists in the blood sample when the number of particles in the ghost characteristic region is greater than the predetermined threshold value; and a warning unit 435 for giving a warning after determining that platelet aggregation exists in the blood sample, wherein the waning is given in a form of text, sound, light or a pop-up window.

Further, the ghost characteristic region determination unit 431 is used for analyzing a ghost region of the fluorescence-scattered light scatterdiagram to determine the ghost characteristic region, wherein the ghost characteristic region is determined based on a position of a white blood cell population region.

Further, the ghost characteristic region determination unit 431 is used for analyzing a ghost region of the fluorescence-scattered light scatterdiagram to determine the ghost characteristic region, wherein the ghost characteristic region is a region in the ghost region in which the scattered light signals are equal to and/or greater than the scattered light signals of a white blood cell population and the fluorescence signals are equal to and/or greater than the fluorescence signals of the white blood cell population.

For more details, reference can be made to the above description of FIGS. 2 to 11, which will not be repeated here.

FIG. 14 is a schematic structure diagram of a detection device in a flow cytometer provided by the present application, the flow cytometer comprising:

a sampling device 1 for drawing a blood sample;

a pretreatment device 2 for pretreating the blood sample so as to obtain a treated blood sample, wherein the pretreatment comprises hemolyzing and fluorescence staining of cells in the blood sample;

a detection device 3 for passing the cells in the treated blood sample one by one through a detection region to detect scattered light signals and fluorescence signals of the cells in the blood sample, wherein the scattered light signals are forward scattered light signals and/or side scattered light signals, and specifically, the detection device 3 detects and collects the forward scattered light signals, the side scattered light signals and the fluorescence signals of the cells in the blood sample in the same channel (i.e., the channel for differentiating between NRBCs and WBCs); and a device 4 for identifying platelet aggregation, used for generating a fluorescence-scattered light scatterdiagram of the blood sample according to the forward scattered light signals, the side scattered light signals and the fluorescence signals detected by the detection device, acquiring a ghost characteristic region of the fluorescence-scattered light scatterdiagram and counting a number of particles in the ghost characteristic region to determine whether the number of particles exceeds a threshold value, and giving a platelet aggregation warning if the number of particles exceeds the threshold value.

Reference can be made to the above description of FIGS. 12 and 13 for more details of the device 4 for identifying platelet aggregation.

By implementing the embodiments of the present application, the following beneficial effects can be achieved:

In the implementation of the present application, a blood sample is pretreated with a reagent, and cells in the blood sample are detected via a flow cytometer so as to obtain scattered light signals and fluorescence signals of the cells. By generating a fluorescence-scattered light scatterdiagram, ghost particles and white blood cells in the blood sample are distinguished from each other, and the number of particles in a specific region within a ghost region is measured to determine whether PLT aggregation exists in the blood sample for identification and warning of PLT aggregation.

In embodiments of the present application, so long as NRBCs and WBCs can be distinguished from each other in the same channel, the identification of PLT aggregation can be carried out by using a specific region in the ghost region without employing a special pretreatment reagent, and a more accurate PLT aggregation warning can be given, thereby providing important information for clinical blood cell analysis in a quick and simple manner without increasing the structure and cost of the instrument system.

It is to be understood that those of ordinary skill in the art would be able to understand that implementation of all or some of the procedure of the exemplary methods described above could be achieved by hardware commanded by a computer program, which program can be stored in a computer-readable storage medium and, when executed, carry out a procedure of the embodiments of the methods described above. Therefore, the present application also provides a computer-readable storage medium, comprising instructions which, when executed on a computer, cause the computer to perform the above-described method for identifying platelet aggregation. The storage medium can be a magnetic disk, an optical disk, a read-only memory (ROM), a random access memory (RAM), etc.

For convenience of description, scatterdiagrams generated by fluorescence and scattered light signals of normal samples and PLT aggregation samples are provided below for illustration, wherein the instrument used is a BC-6800 cell analyzer of Shenzhen Mindray Bio-Medical Electronics Co., Ltd., and the compound described in Embodiment 10 of Chinese Patent CN 200910238927 is used as the fluorescent dye.

Embodiment I

In a scatterdiagram consisting of fluorescence and forward scattered light, a ghost region of a normal sample shown in FIG. 2 is located in a region with lower fluorescence signals and lower forward scattered light signals compared with a PLT aggregation sample shown in FIG. 3. Signal points with forward scattered light signals equal to or greater than those of white blood cell population and signal points with fluorescence signals equal to or greater than those of the white blood cell population are selected as a ghost characteristic region. The number of ghost particles in this region is counted and if the number is greater than a certain number, a PLT aggregation warning will be given. In this embodiment, the warning threshold is set as 55 points.

In order to further confirm the effect of the provided method for identifying platelet aggregation, the applicant herein conducted a comparative experiment.

Figure 5:
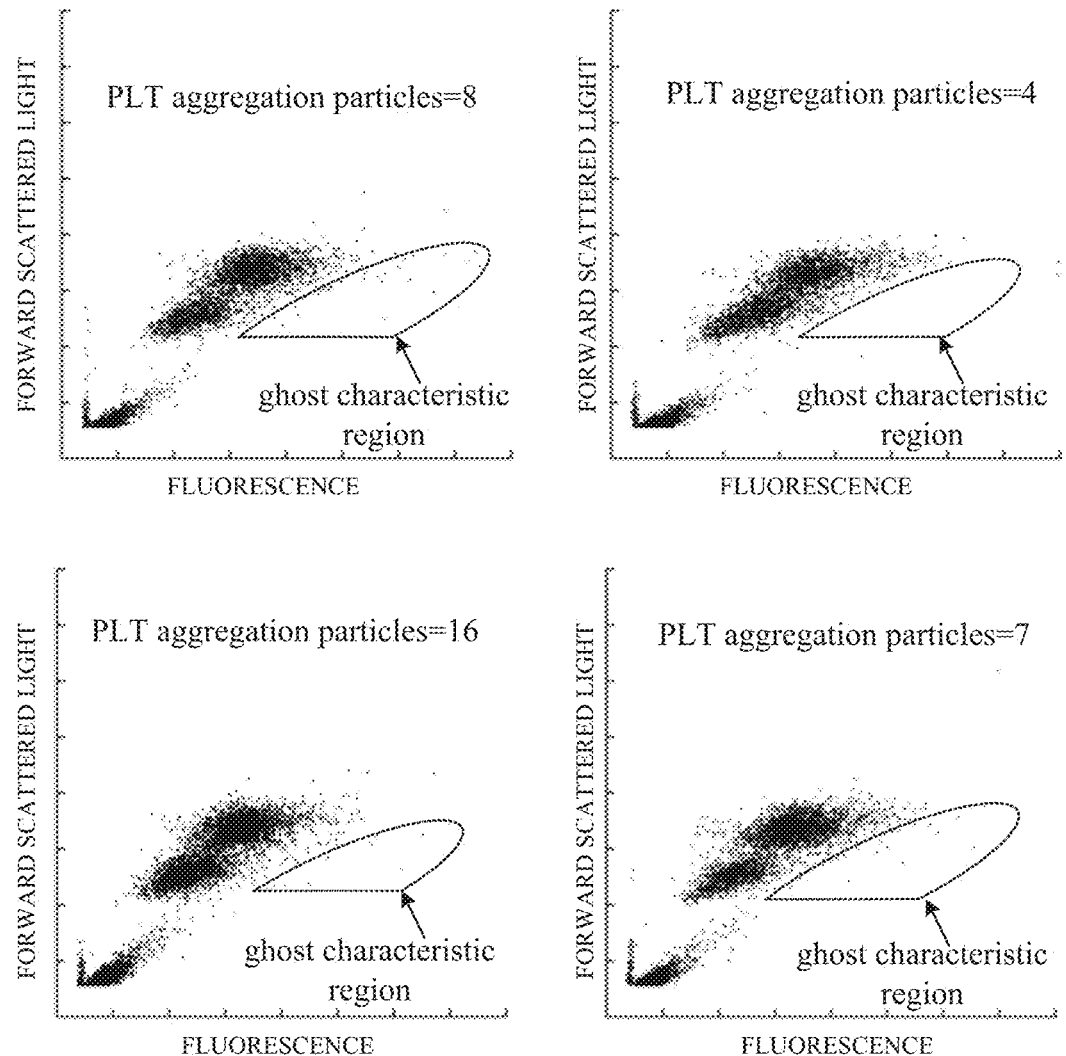
FIG. 5 shows the counts of particles in a PLT aggregation region of four normal samples in a forward scattered light view.

As shown in FIG. 5, four normal samples were randomly selected and no PLT aggregation was found by manual microscopic examination of blood smears. Tests were carried out according to the platelet aggregation identification method described in this application, and the numbers of ghost particles in the ghost characteristic regions of the 4 normal samples were 8, 4, 16 and 7, respectively, which did not reach the warning threshold of 55, and no PLT aggregation warning was given for any of the 4 samples.

Twenty-eight PLT aggregation samples were randomly selected, and PLT aggregation was found in all of them by manual microscopic examination of blood smears. Tests were carried out according to the platelet aggregation identification method described in this application, and the results of the counted number of particles in the ghost characteristic region of the 28 PLT aggregation samples are shown in Table 1.

TABLE 1

Number of Particles in Ghost Characteristic Region in BC-6800 Fluorescence-Forward scattered light View of 28 Samples

| Sample No. | Number of Particles in Ghost Characteristic Region |
| --- | --- |
| Sample 1 | 518 |
| Sample 2 | 650 |
| Sample 3 | 145 |
| Sample 4 | 728 |
| Sample 5 | 902 |
| Sample 6 | 83 |
| Sample 7 | 1297 |
| Sample 8 | 127 |
| Sample 9 | 704 |
| Sample 10 | 445 |
| Sample 11 | 1284 |
| Sample 12 | 583 |
| Sample 13 | 112 |
| Sample 14 | 683 |
| Sample 15 | 185 |
| Sample 16 | 57 |
| Sample 17 | 129 |
| Sample 18 | 1251 |
| Sample 19 | 171 |
| Sample 20 | 619 |
| Sample 21 | 71 |
| Sample 22 | 168 |
| Sample 23 | 112 |
| Sample 24 | 87 |
| Sample 25 | 424 |
| Sample 26 | 453 |
| Sample 27 | 421 |
| Sample 28 | 584 |

TABLE 1-continued

Figure 6:
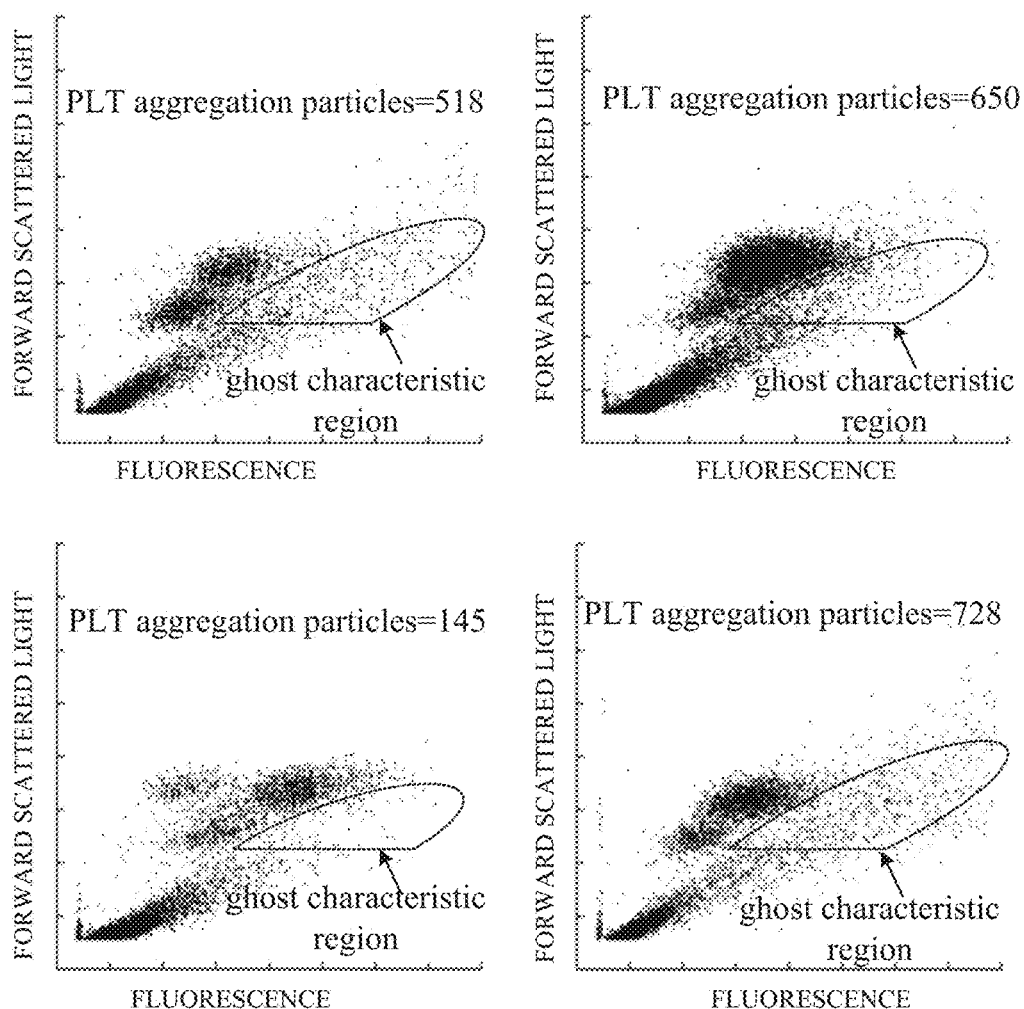
FIG. 6 shows the counts of particles in a PLT aggregation region of four PLT aggregation samples in a fluorescence-forward scattered light view.

Number of Particles in Ghost Characteristic Region in BC-6800 Fluorescence-Forward scattered light View of 28 Samples The results showed that the PLT aggregation particles in the ghost characteristic region of the 28 PLT aggregation samples all exceeded the warning threshold of 55 points and thus a PLT aggregation warning was given. Among them, the fluorescence-forward scattered light scatterdiagrams of PLT aggregation samples No. 1-4 are shown in FIG. 6. The numbers of ghost particles in the ghost characteristic regions of the 4 PLT aggregation samples No. 1-4 were 518, 650, 145 and 728, respectively, which exceeded the warning threshold of 55, and a PLT aggregation warning was given for all of the 4 samples.

Embodiment II in a scatterdiagram consisting of fluorescence and side scattered light, a ghost region of a normal sample shown in FIG. 7 is located at a lower end of the fluorescence and side scattered light signals compared with a PLT aggregation sample shown in FIG. 8. Signal points with side scattered light signals equal to or greater than those of white blood cell population and signal points with fluorescence signals equal to or greater than those of the white blood cell population are selected as a ghost characteristic region. The number of particles in this region is counted and if the number is greater than a certain number, a PLT aggregation warning will be given. In this embodiment, the warning threshold is set as 50 points.

In order to further confirm the effect of the provided method for identifying platelet aggregation, the applicant herein conducted a comparative experiment.

Figure 10:
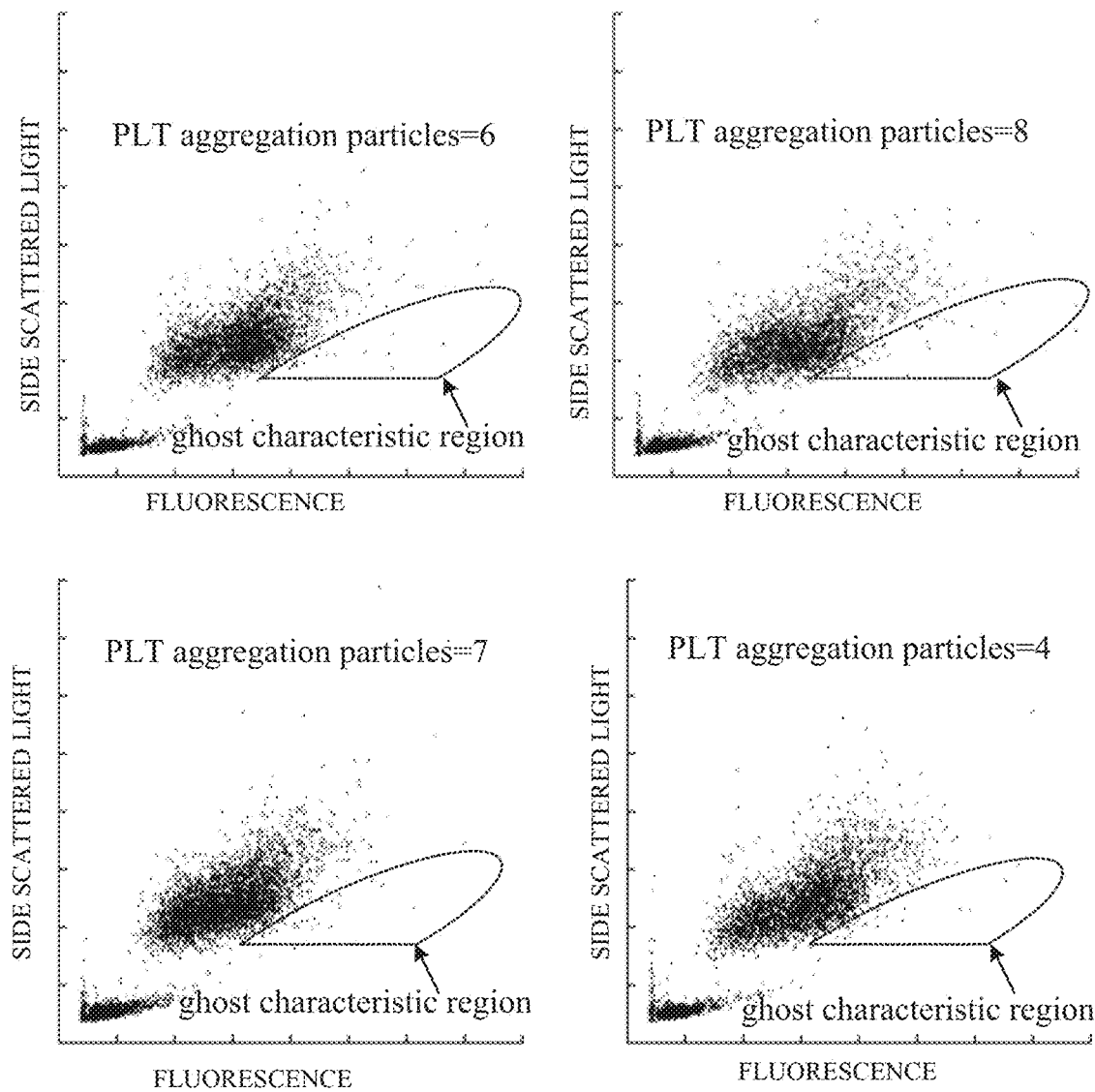
FIG. 10 shows the counts particles in a PLT aggregation region of four normal samples in a side scattered light view.

As shown in FIG. 10, four normal samples were randomly selected and no PLT aggregation was found by manual microscopic examination of blood smears. Tests were carried out according to the platelet aggregation identification method described in this application, and the numbers of ghost particles in the ghost characteristic regions of the 4 normal samples were 6, 8, 7 and 1, respectively, which did not reach the warning threshold of 50, and PLT aggregation warning was not given for any of the 4 samples.

Twenty-eight PLT aggregation samples were randomly selected, and PLT aggregation was found in all of them by manual microscopic examination of blood smears. Tests were carried out according to the platelet aggregation identification method described in this application, and the results of the counted number of particles in the ghost characteristic region of the 28 PLT aggregation samples are shown in Table 2.

TABLE 2

Number of Particles in PLT Aggregation Region in BC-6800
Fluorescence-Side scattered light View of 28 Samples

| Sample No. | Number of Particles in Ghost Characteristic Region |
|---|---|
| Sample 1 | 502 |
| Sample 2 | 585 |
| Sample 3 | 120 |
| Sample 4 | 711 |
| Sample 5 | 873 |
| Sample 6 | 52 |
| Sample 7 | 1294 |
| Sample 8 | 91 |
| Sample 9 | 685 |
| Sample 10 | 428 |
| Sample 11 | 1238 |
| Sample 12 | 545 |
| Sample 13 | 65 |
| Sample 14 | 643 |
| Sample 15 | 177 |
| Sample 16 | 60 |
| Sample 17 | 100 |
| Sample 18 | 1250 |
| Sample 19 | 136 |
| Sample 20 | 610 |
| Sample 21 | 51 |
| Sample 22 | 145 |
| Sample 23 | 113 |
| Sample 24 | 77 |
| Sample 25 | 378 |
| Sample 26 | 424 |
| Sample 27 | 415 |
| Sample 28 | 580 |

Figure 11:
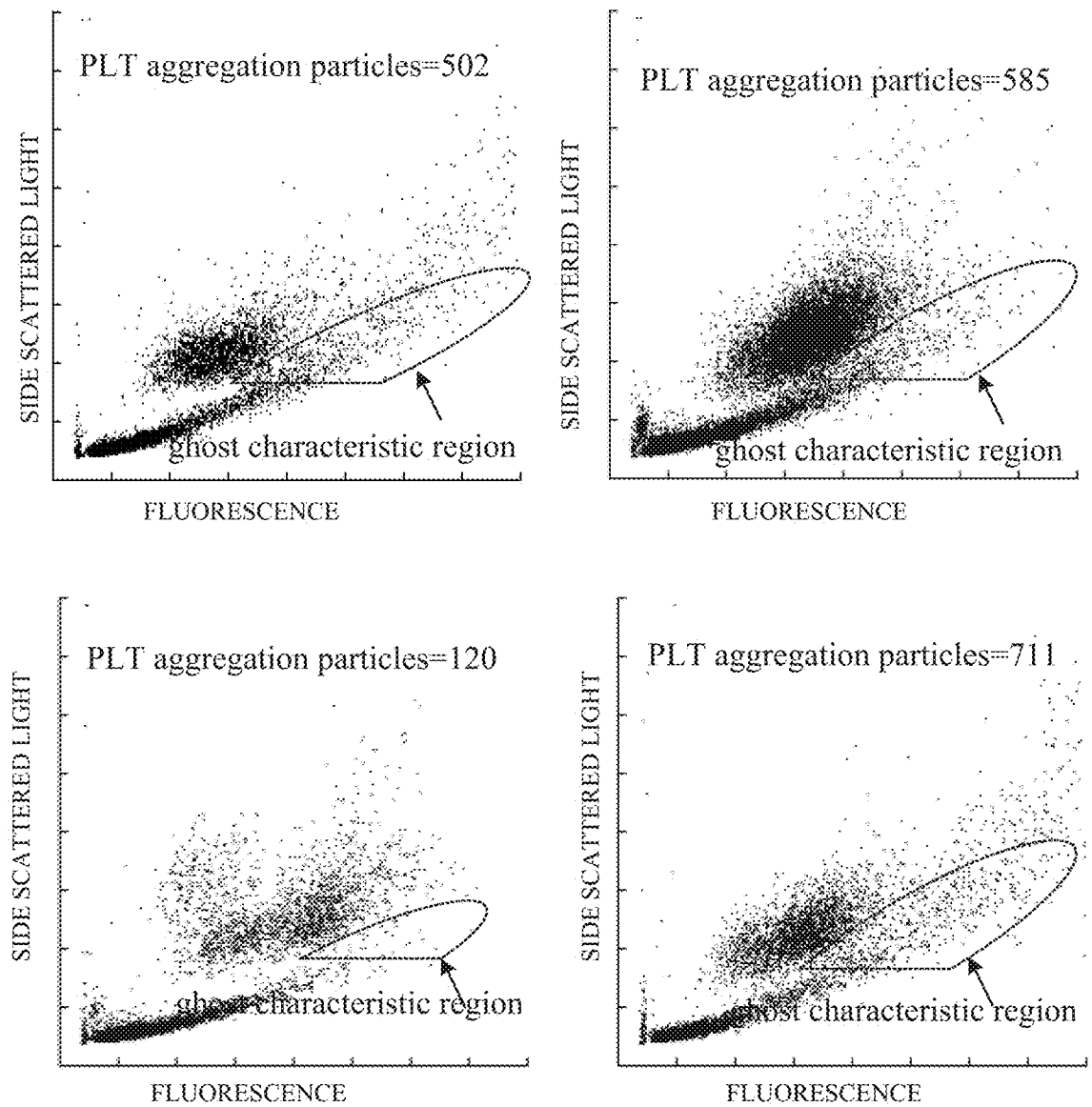
FIG. 11 shows the counts of particles in a PLT aggregation region of four PLT aggregation samples in a fluorescence-side scattered light view.

The results showed that the PLT aggregation particles in the ghost characteristic region of the 28 PLT aggregation samples all exceeded the warning threshold of 50 points and thus a PLT aggregation warning was given. Among them, the fluorescence-side scattered light scatterdiagrams of PLT aggregation samples No. 1-4 are shown in FIG. 11. The numbers of ghost particles in the ghost characteristic regions of the 4 PLT aggregation samples were 502, 585, 120 and 711, respectively, which exceeded the warning threshold of 50, and a PLT aggregation warnings was given for all of the 4 samples.

The above results show that the method for identifying platelet aggregation described in the present application has high warning sensitivity and specificity and satisfying warning accuracy for PLT aggregation warning.

The above only describes some of the embodiments of the present invention and it should be noted that, for a person of ordinary skill in the art, improvements and modifications can be made without departing from the principles of the present invention, which improvements and modifications should also be considered to be within the scope of protection of the present invention.

The invention claimed is:

1. A method for identifying platelet aggregation, comprising the steps of:
pretreating cells in a blood sample, wherein the pretreatment comprises hemolyzing and fluorescence staining;
passing the cells in the pretreated blood sample one by one through a detection region of a flow cytometer, so as to acquire scattered light signals and fluorescence signals of the cells in the blood sample, wherein the scattered light signals are forward scattered light signals or side scattered light signals;
differentiating between a ghost region and a white blood cell region by using a fluorescence-scattered light scattergram generated by the scattered light signals and the fluorescence signals of the cells in the blood sample; and
counting a number of particles in a ghost characteristic region in the fluorescence-scattered light scattergram of the blood sample to determine whether the number of particles exceeds a threshold value, and outputting a warning of platelet aggregation if the number of particles exceeds the threshold value;
wherein the scattered light signals of the ghost characteristic region are greater than or equal to a minimum scattered light signal of the white blood cell region, and the fluorescence signals of the ghost characteristic region are greater than or equal to a minimum fluorescence signal of the white blood cell region; or
wherein the scattered light signals of the ghost characteristic region are greater than or equal to the minimum scattered light signal of the white blood cell region and less than or equal to a maximum scattered light signal of the white blood cell region.

2. The method of claim 1, further comprising:
differentiating between the ghost region, the white blood cell region and a nucleated red blood cell region by using the fluorescence-scattered light scattergram.

3. The method of claim 1, wherein the ghost characteristic region is a part of the ghost region.

4. The method of claim 3, wherein the scattered light signals of the ghost characteristic region are greater than a specific signal value, or the fluorescence signals of the ghost characteristic region are greater than a specific signal value.

5. The method of claim 4, wherein the ghost characteristic region is determined based on a position of the white blood cell region.

6. The method of claim 5, wherein the scattered light signals of the ghost characteristic region are greater than or equal to the maximum scattered light signal of the white blood cell region, and the fluorescence signals of the ghost characteristic region are greater than or equal to a maximum fluorescence signal of the white blood cell region.

7. The method of claim 5, wherein
the fluorescence signals of the ghost characteristic region are greater than or equal to the minimum fluorescence signal of the white blood cell region and less than or equal to a maximum fluorescence signal of the white blood cell region.

8. The method of claim 1, wherein the threshold value is preset according to the selection of the ghost characteristic region.

9. A non-transitory computer-readable storage medium, comprising instructions which, when executed on a computer, cause the computer to perform the method of claim 1.

10. A cell analyzer, comprising:
a sampling device for drawing a blood sample;
a pretreating device for pretreating the blood sample so as to obtain a treated blood sample, wherein the pretreating comprises hemolyzing and fluorescence staining of cells in the blood sample;
a detection device for passing the cells in the treated blood sample one by one through a detection region to detect scattered light signals and fluorescence signals of the cells in the blood sample, wherein the scattered light signals are forward scattered light signals and/or side scattered light signals; and
a processor, wherein the processor is programmed with and executes processor-executable instructions to: generate a fluorescence-scattered light scattergram of the blood sample according to the forward scattered light signals, the side scattered light signals and the fluorescence signals detected by the detection device, acquire a ghost characteristic region in the fluorescence-scattered light scattergram and count a number of particles in the ghost characteristic region to determine whether the number of particles exceeds a threshold value, and output a warning of platelet aggregation if the number of particles exceeds the threshold value;

wherein the processor is configured to determine a region, where the scattered light signals of the region are greater than or equal to a minimum scattered light signal of a white blood cell region and the fluorescence signals of the region are greater than or equal to a minimum fluorescence signal of the white blood cell region, as the ghost characteristic region; or wherein the processor is configured to determine a region, where the scattered light signals of the region are greater than or equal to the minimum scattered light signal of the white blood cell region and less than or equal to a maximum scattered light signal of the white blood cell region, as the ghost characteristic region.

11. The analyzer of claim 10, wherein the processor is further configured to differentiate between a ghost region, the white blood cell region and a nucleated red blood cell region by using the fluorescence-scattered light scattergram.

12. The analyzer of claim 11, wherein the ghost characteristic region is a part of the ghost region.

13. The analyzer of claim 12, wherein the scattered light signals of the ghost characteristic region are greater than a specific signal value, or the fluorescence signals of the ghost characteristic region are greater than a specific signal value.

14. The analyzer of claim 13, wherein the ghost characteristic region is determined based on a position of the white blood cell region.

15. The analyzer of claim 14, wherein the scattered light signals of the ghost characteristic region are greater than or equal to the maximum scattered light signal of the white blood cell region, and the fluorescence signals of the ghost characteristic region are greater than or equal to a maximum fluorescence signal of the white blood cell region.

16. The analyzer of claim 14, wherein
the fluorescence signals of the ghost characteristic region are greater than or equal to the minimum fluorescence signal of the white blood cell region and less than or equal to a maximum fluorescence signal of the white blood cell region.

17. The analyzer of claim 10, wherein the threshold value is preset according to the selection of the ghost characteristic region.

* * * * *